(12) United States Patent
Cannon et al.

(10) Patent No.: US 11,367,518 B1
(45) Date of Patent: Jun. 21, 2022

(54) CONTROLLED SUBSTANCE FRAUD PREVENTION METHOD

(71) Applicants: Billy Cannon, Stanley, WI (US); James M. Moran, Stanley, WI (US)

(72) Inventors: Billy Cannon, Stanley, WI (US); James M. Moran, Stanley, WI (US)

( * ) Notice: Subject to any disclaimer, the term of this patent is extended or adjusted under 35 U.S.C. 154(b) by 0 days.

(21) Appl. No.: 17/207,075

(22) Filed: Mar. 19, 2021

Related U.S. Application Data

(60) Provisional application No. 63/101,121, filed on Apr. 20, 2020.

(51) Int. Cl.
| | |
|---|---|
| *G16H 20/13* | (2018.01) |
| *G07C 9/00* | (2020.01) |
| *G06F 21/32* | (2013.01) |
| *G06V 40/16* | (2022.01) |
| *B65D 83/04* | (2006.01) |
| *A61J 1/03* | (2006.01) |

(52) U.S. Cl.
CPC ............ *G16H 20/13* (2018.01); *G06F 21/32* (2013.01); *G06V 40/172* (2022.01); *G07C 9/00563* (2013.01); *A61J 1/03* (2013.01); *B65D 83/0409* (2013.01)

(58) Field of Classification Search
CPC .... G16H 20/13; G07C 9/00563; G06F 21/32; G06V 40/172; B65D 83/0409; A61J 1/03
See application file for complete search history.

(56) References Cited

U.S. PATENT DOCUMENTS

| | | | |
|---|---|---|---|
| 8,190,291 B2 | 5/2012 | Beane et al. | |
| 2006/0265102 A1 | 11/2006 | Bain | |
| 2013/0070090 A1* | 3/2013 | Bufalini | G16H 20/13 348/143 |
| 2017/0221060 A1 | 8/2017 | Boyd et al. | |
| 2018/0280243 A1* | 10/2018 | Velani | A61J 7/0472 |
| 2019/0240113 A1* | 8/2019 | Velani | A61J 7/0418 |

* cited by examiner

*Primary Examiner* — Michael Collins
(74) *Attorney, Agent, or Firm* — Donald J. Ersler

(57) ABSTRACT

A controlled substance fraud prevention method preferably includes a camera, a database of faces with names, facial recognition software, a database of medicines prescribed to each face and a portable medicine safe. A patient goes to a doctor for some medical issue. The doctor will issue a prescription for a controlled substance, after photographing a face of the patient; and uploading the facial image to a computer server. The first computer server contains a database of faces and names. Facial recognition software will compare the uploaded face to other faces to determine if there are other names with the same face. A photograph of the patient's face is taken at the pharmacy and the image is uploaded to the computer server by pharmacist for facial recognition. The pharmacist also checks a database of names and medicines, before providing the prescription through a portable pill or liquid medicine safe.

18 Claims, 5 Drawing Sheets

CONTROLLED SUBSTANCE FRAUD PREVENTION METHOD

CROSS-REFERENCE TO RELATED APPLICATIONS

This is a utility patent application which claims the benefit of provisional patent application No. 63/101,121 filed on Apr. 20, 2020, which is hereby incorporated by reference in its entirety.

BACKGROUND OF THE INVENTION

1. Field of the Invention

The present invention relates generally to drug abuse and more specifically to a controlled substance fraud prevention method, which makes it more difficult for someone to fraudulently obtain and abuse controlled substances.

2. Discussion of the Prior Art

There has been an epidemic of opiate abuse in the United States and around the world that has been going on for many years. There are many reasons why the problem is so bad, such as drug companies making excessive profits from the diversion of pain medications; doctors who made extra income from excessively prescribing these medications; patients abusing the medications and; selling the medications for profit in the black market. There have been some attempts to mitigate the prescription drug problem, but it is mostly done by law enforcement actions, against doctors who prescribe the medications; and arresting drug addicts, who abuse the prescription medications. Opioid abuse is costly in terms of taxpayer money for law enforcement, and the cost in human lives and suffering. Further, there are civil actions initiated by the government to punish the companies who illegally profited from the excess distribution of these medications.

Many of the problems that exist with opiate medications is the fact that many of these medications are abused by the patients who need to take the opiate medications. If the patients take more medication than what is prescribed or they take their medications sooner or more often than prescribed by the doctor, there will soon be a supply problem. The overconsumption of the medication will eventually lead to the patients needing more medication to ease their pain or it will lead to outright addiction. If these patients are not able to procure enough medication for their addiction, they will invariably turn to illegal opiates (like heroin) to quench their addiction. In a lot of circumstances the patients lose their jobs, as they become addicts. Thereby, they cannot take care of their children, financially, as well as emotionally, as their addiction becomes all consuming. Many of the addicts must resort to illegal conduct like stealing, robbery, burglary, prostitution, etc. . . . . . All of which, have a corrosive effect upon society, driving up crime rates, creating victims of crimes perpetrated by the drug addicts in their attempt to get the money for the illegal drugs that they crave and need to sustain their addiction. The fact remains that many of the aforementioned problems still exist and have not been adequately solved to prevent this problem from reemerging.

There are systems that purport to stop medication fraud, but they simply rely upon the honesty of patients, doctors, and drug companies to do the right thing, which is hardly a safeguard. These systems maintain databases of patients names, supplied by the patient, with or without proof of identification, even with proof of identification, identification cards are easily altered, and in some cases criminals have stolen identification card making equipment to make their own fake id cards. Therefore, self-identifying patients or even patients presenting identification documents can game the system. They simply present multiple identification cards with multiple names to different doctors, to get multiple prescriptions for medications that are commonly abused. Many doctors are very busy and seeing patients at a dizzying pace, spending no more than a few minutes with each patient. Therefore, this type of fraud is not easily policed by doctors, who are already very busy, and giving patients the benefit of doubt that there conditions are as described and that they are who they purport to be.

In many cases, this is not the case. Many of these patients are drug addicts, and would do almost anything to get the drugs that they crave. In addition, some of the problems that exist are not the fault of the patients who were prescribed the opiate medication, but with people that may live with them or visit them, etc. . . . . . These people may simply steal the patients pain medication without their knowledge or consent. In most instances, these pain medications are simply stored in a medicine cabinet in the person's bathroom. Once these medications are stolen, they are either taken by the person who stole them, or the person sells these pain medications on the black market to drug dealers, who in turn, sells them for cash, trades them for stolen property, or barters them for sexual favors, with drug addicts.

Patent publication no. 2006/0265102 to Bain discloses an automated prescription dispensing system and method of use. U.S. Pat. No. 8,190,291 to Beane et al. discloses an automated vending of products containing controlled substances. Patent publication no. 2017/0221060 to Boyd et al. discloses an authenticated purchase of restricted items.

Accordingly, there is a clearly felt need in the art for a controlled substance fraud prevention method, which uses database verification to ensure that the correct person is obtaining controlled substances from one doctor and one pharmacy; and which provides a safe for dispensing only one dose at a time to prevent addiction to controlled substances.

SUMMARY OF THE INVENTION

The present invention provides a controlled substance fraud prevention method, which makes it more difficult for someone to fraudulently obtain controlled substances. The controlled substance fraud prevention method preferably includes at least one camera, a database of faces with names, facial recognition software, a database of medicines prescribed to each face and a portable medicine safe. A patient goes to a doctor to complain of some type of medical issue that they are having. The doctor examines the patient. The doctor will issue a prescription for a controlled substance, if the doctor feels that the controlled substance will help the patient. Before sending the prescription to a pharmacy doctor will photograph the patients face with a camera. The image of the face is uploaded to the database of faces with names. The facial recognition software will analyze the face to see, if the face is associated with more than one name. If the face is associated with only one name, the patient will be issued the prescription. If the face is associated with more than one name, the patient will be denied the prescription. The patient will have the ability to challenge facial recognition software identification.

The patient goes to the pharmacy to pick-up their medicine. A photograph of the patient's face is taken again. The face may also be that of a legally designated individual. The image of the face is uploaded to the database of faces with names to see if the face is associated with the name given to the pharmacist. The facial recognition software will analyze the face to see, if the face is associated with more than one name. The pharmacist will also check the database of medicines prescribed to each face to see if face has a prescription from more than one doctor. If the face is associated with only one name and there are not multiple prescriptions for the same medicine, the pharmacist will provide the controlled substance in the portable medicine safe, if the medicine is susceptible to abuse. If the face does not match the name or if there are multiple prescriptions for the same medicine, the new prescription will be denied.

The portable medicine safe preferably includes a housing, a dispensing mechanism, an external lock and an internal lock. The housing includes an internal cavity and a bottom dispenser opening. The dispensing mechanism is loaded with single doses of medicine in pill form or liquid form by a pharmacist. The dispensing mechanism is inserted into the bottom dispenser opening. The dispensing mechanism is locked in the portable medicine safe with the external lock, which engages a portion of the dispensing mechanism. The external lock is preferably a key lock. The internal lock includes a smart device, such as a smart phone and an internal lock. The smart phone is mounted to a front of the housing. The smart phone includes a touch screen for entering an access code, a camera and an access code application. The dispensing mechanism cannot be removed, unless the external lock is opened and a special access code is entered into the smart phone both by the pharmacist. The access code application is used to transmit a signal to the internal lock to unlock thereof. The patient takes the portable medicine safe back to their home from the pharmacy. The patient receives a dose of medicine by holding the camera in the smart device in front of their face at about the time of their dosage. It could also be required that the patient enter an access code into the smart device, before the dosage is dispensed. The dispensing device will dispense a single dosage of medicine, after verifying that the patient appeared in front of the camera at the correct time.

Accordingly, it is an object of the present invention to provide a controlled substance fraud prevention method, which uses database verification to ensure the correct person is obtaining controlled substances from one doctor and one pharmacy.

Finally, it is another object of the present invention to provide a controlled substance fraud prevention method, which provides a safe for dispensing only one dose at a time to prevent addiction to controlled substances.

These and additional objects, advantages, features and benefits of the present invention will become apparent from the following specification.

DETAILED DESCRIPTION OF THE PREFERRED EMBODIMENTS

Figure 1:
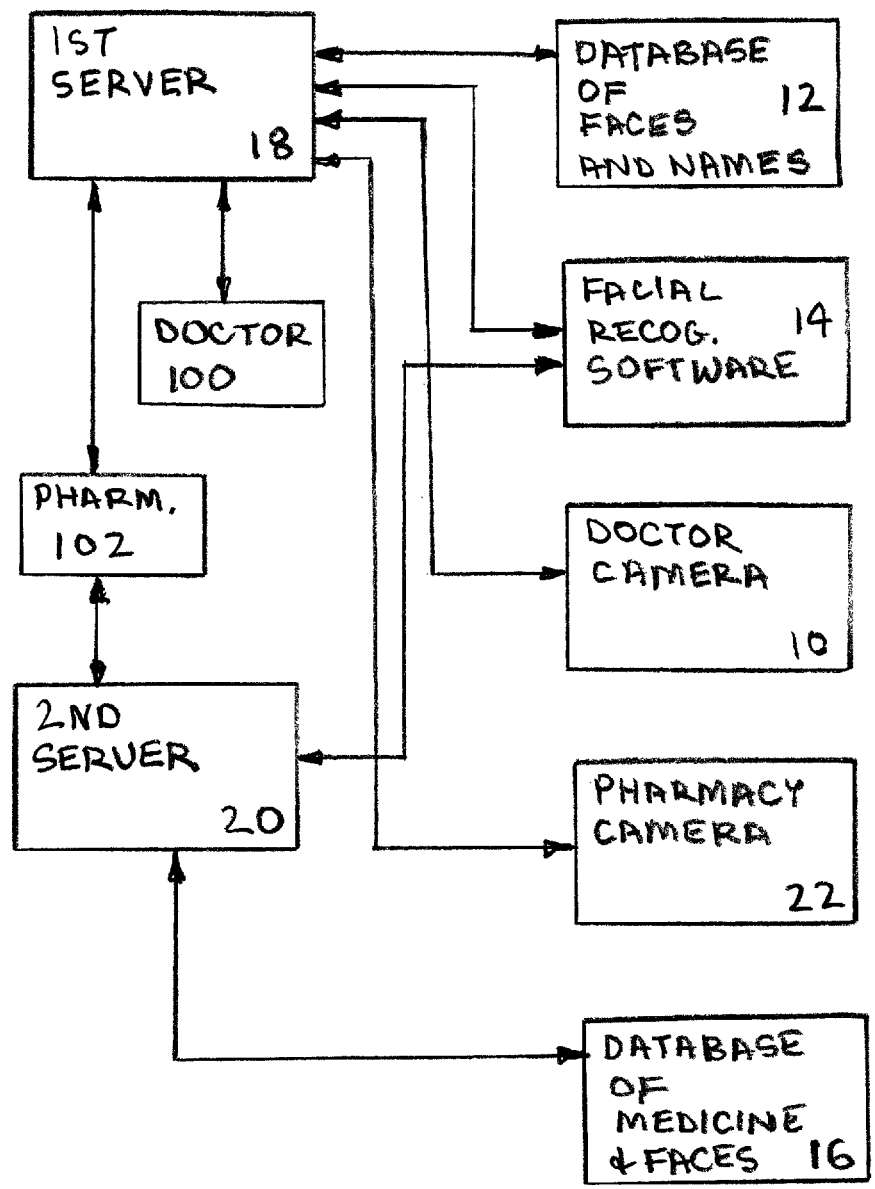
FIG. 1 is a schematic diagram of elements of a controlled substance fraud prevention method in accordance with the present invention.

With reference to FIG. 1, a controlled substance fraud prevention method 1 is shown. The control substance fraud prevention method preferably includes a doctor camera 10, a database of faces with names 12, facial recognition software 14, a database of medicines prescribed to each face 16, a pharmacy camera 22 and a portable medicine safe 24, 26. The database of faces with names 12 and the database of facial recognition software 14 are both retained on a first computer server 18. The doctor camera 10 is connected to the first computer server 18. The database of medicines prescribed to each face 16 is preferably retained on a second computer server 20, but could be retained the first computer server 18. A patient goes to a doctor to complain of some type of medical issue that they are having. The doctor examines the patient. The doctor will issue a prescription for a controlled substance, if the doctor feels that the controlled substance will help the patient. Before sending the prescription to a pharmacy, the doctor will photograph the patients face with the doctor camera 10. The doctor (or one of the staff) 100 uploads the image of the face to the first computer server 16, which includes the database of faces with names 12. The facial recognition software 14 will analyze the face to see, if the face is associated with more than one name. If the face is associated with only one name, the patient will be issued the prescription. If the face is associated with more than one name, the patient will be denied the prescription. The patient will have the ability to challenge the facial recognition software identification.

The patient goes to the pharmacy to pick-up their medicine. A photograph of the patient's face is taken with a pharmacy camera 22. The face may also be that of a legally designated individual. The pharmacist (or one of the staff) 102 uploads the image of the face to the first computer server 18 to see if the face is associated with the name given to the pharmacist 102 according to the database of faces with names 12. The facial recognition software 14 will analyze the face to see, if the face is associated with more than one name. The pharmacist will also access the second computer server 20 to see if the database of medicines prescribed to each face 16 to confirm there are not prescriptions from more than one doctor.

Figure 2:
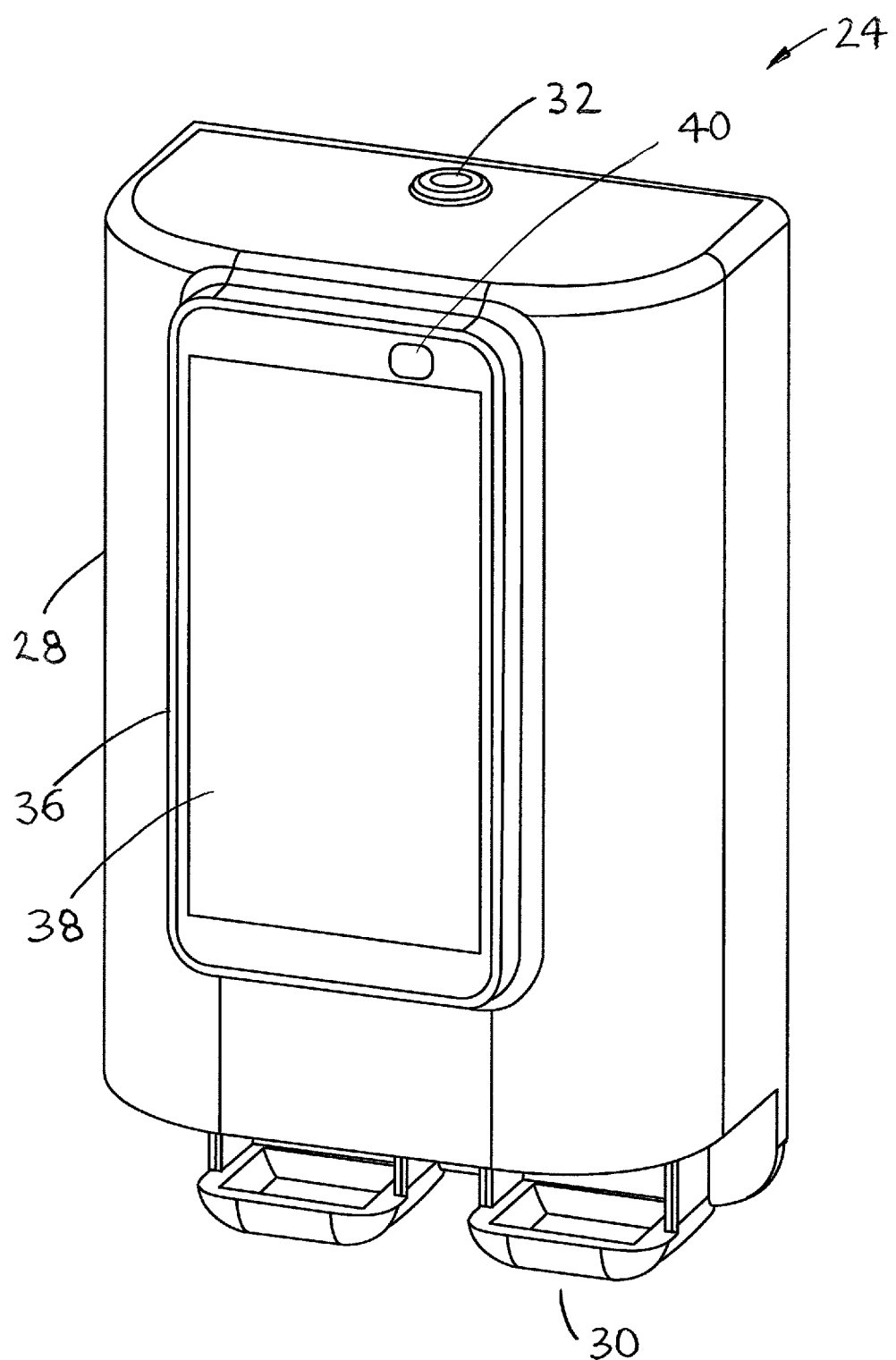
FIG. 2 is a perspective view of a portable pill medicine safe in accordance with the present invention.
Figure 4:
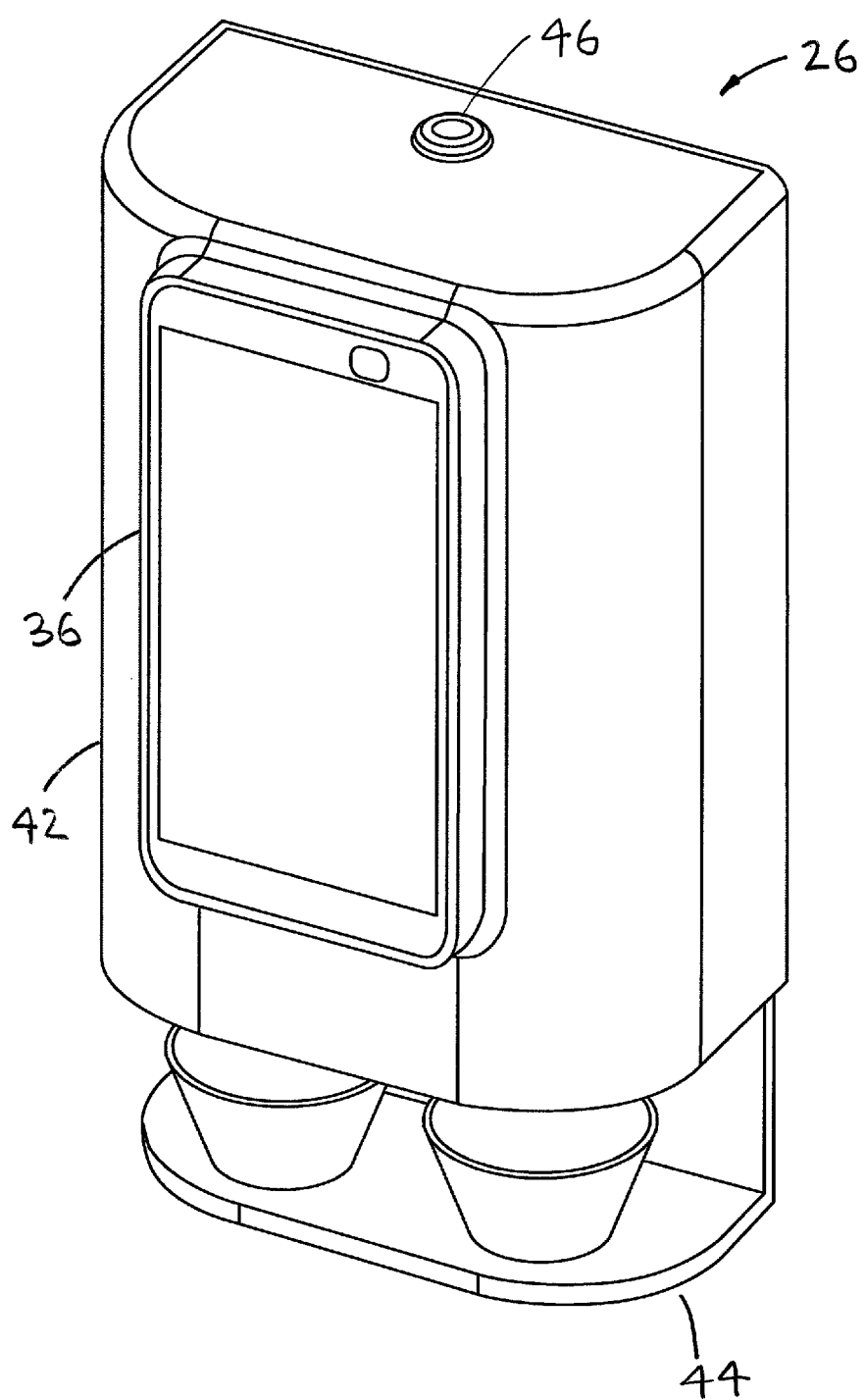
FIG. 4 is a perspective view of a portable liquid medicine safe in accordance with the present invention.

With reference to FIGS. 2 and 4, if the face is associated with only one name and there are not multiple prescriptions for the same medicine, the pharmacist will provide the controlled substance in either a portable pill medicine safe 24 or a portable liquid medicine safe 26, if the medicine is susceptible to abuse. If the face does not match the name or if there are multiple prescriptions for the same medicine, the new prescription will be denied.

Figure 3:
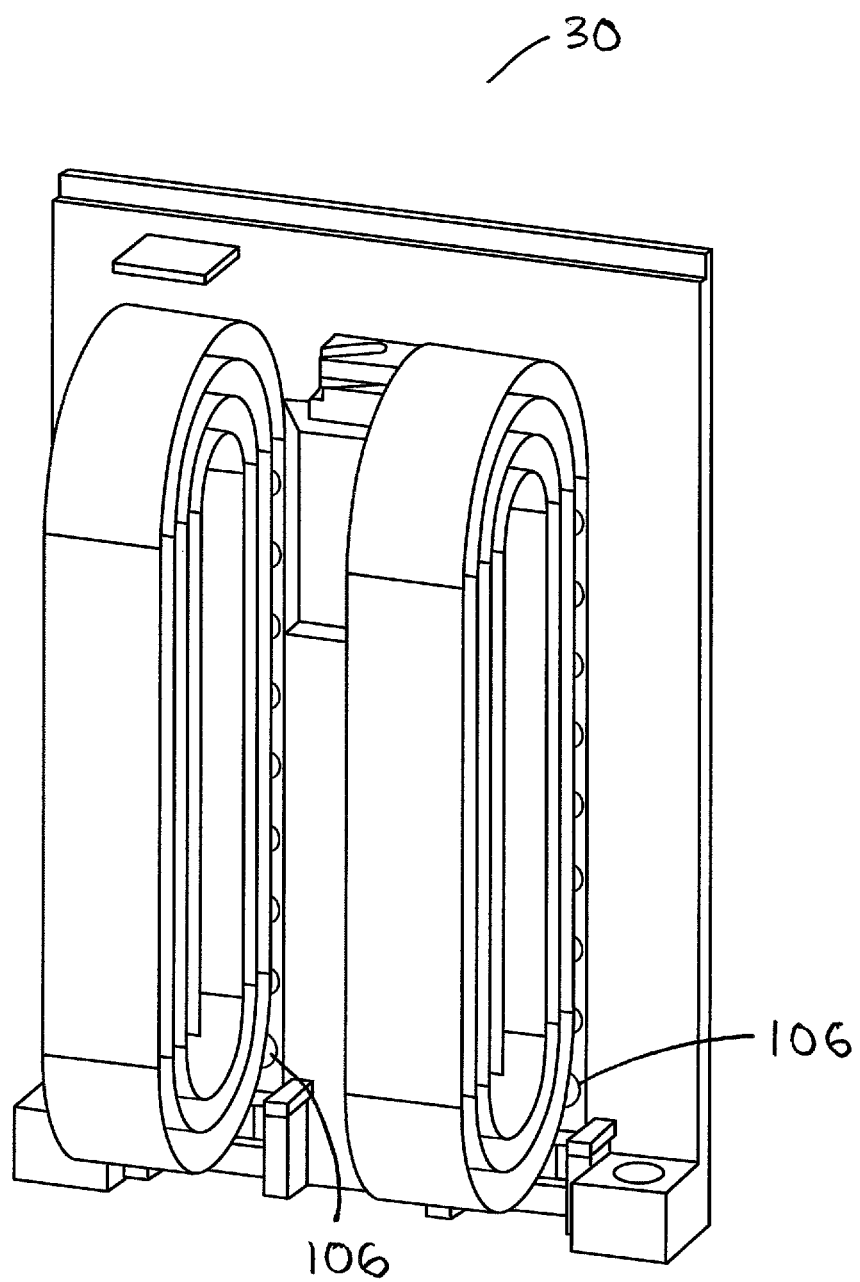
FIG. 3 is a perspective view of a dispensing mechanism of a portable pill medicine safe in accordance with the present invention.

With reference to FIGS. 2-3, the pill portable medicine safe 24 preferably includes a housing 28, a pill dispensing mechanism 30, an external lock 32 and an internal lock. The housing 28 includes an internal cavity and a bottom dispenser opening. The pill dispensing mechanism 30 is loaded with single doses of pills 106. Only the pharmacist can load the pill portable medicine safe 24. The pill dispensing mechanism 30 is inserted into the bottom dispenser opening in the housing 28. The pill dispensing mechanism 30 is locked in the housing 28 with the external lock 32, which engages a portion of the pill dispensing mechanism 30. The external lock 32 is preferably a key lock. The internal lock preferably includes a smart device 36 and an internal lock mechanism (not shown). The smart device 36 is mounted to a front of the housing 28. The smart device 36 includes a touch screen 38 for entering an access code, a camera 40 and an access code application. The pill dispensing mechanism 30 cannot be removed, unless the external lock 32 is opened and a special access code is entered into the smart device 36 only by the pharmacist. The access code application is used to transmit a signal to the internal lock mechanism to unlock thereof.

Figure 5:
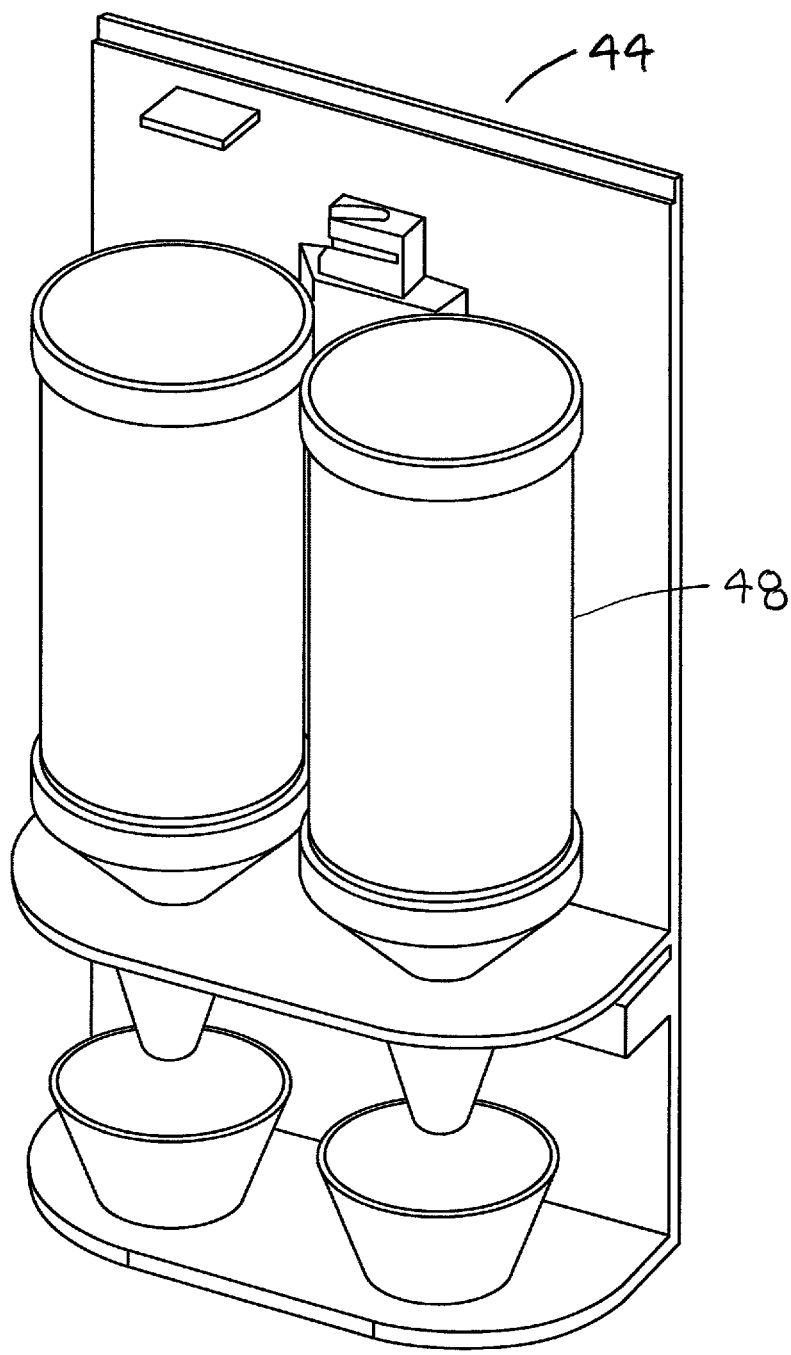
FIG. 5 is a perspective view of a dispensing device of a portable liquid medicine safe in accordance with the present invention.

With reference to FIGS. 4-5, the pill portable medicine safe 26 preferably includes a housing 42, a pill dispensing mechanism 44, an external lock 46 and an internal lock. The housing 42 includes an internal cavity and a bottom dispenser opening. The pill dispensing mechanism 44 is loaded with at least one dispensing bottle 48. Only the pharmacist can load the at least one dispensing bottle 48. The liquid dispensing mechanism 44 is inserted into the bottom dispenser opening in the housing 42. The liquid dispensing mechanism 44 is locked in the housing 42 with the external lock 46, which engages a portion of the liquid dispensing mechanism 44. The external lock 46 is preferably a key lock. The internal lock preferably includes the smart device 36 and an internal lock mechanism. The smart device 36 is mounted to a front of the housing 42. The liquid dispensing mechanism 46 cannot be removed, unless the external lock 46 is opened and a special access code is entered into the smart device 36 only by the pharmacist. The access code application is used to transmit a signal to the internal lock mechanism to unlock thereof.

The patient takes the portable medicine 24, 26 safe back to their home from the pharmacy. The patient receives a dose of medicine by holding the camera 40 in the smart device 36 in front of their face at about the time of their medicine dosage. It could also be required that the patient enter an access code into the smart device 36, before the medicine dosage is dispensed. The dispensing mechanism 30, 44 will dispense a single medicine dosage, after verifying that the patient appeared in front of the camera 40 at the correct time.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

We claim:

1. A controlled substance fraud prevention method comprising the steps of:
    photographing a patient with a camera to obtain a facial image;
    providing a computer server including facial recognition software and a database of names and faces, uploading said facial image with a name to said computer server, said facial recognition software compares said facial image and name with said database of names and faces, said facial recognition software determining if said facial image is associated with more than one name to prevent the patient from having more than one name associated with the same face in said database of names and faces; and
    providing a portable medicine safe to a patient who has only one name associated with their facial, said portable medicine safe includes a housing and a dispensing mechanism, a representative of a pharmacy fills said dispensing mechanism with a controlled substance, said dispensing mechanism is locked in said housing, said dispensing mechanism dispenses dosages of the controlled substance.

2. The controlled substance fraud prevention method of claim 1, further comprising the step of:
    said portable medicine safe includes a smart device with a camera, said camera must capture an image of the patient before dispensing a dose of the medicine.

3. The controlled substance fraud prevention method of claim 1, further comprising the step of:
    entering an access code into said smart device to unlock said dispensing mechanism from said housing.

4. The controlled substance fraud prevention method of claim 1, further comprising the step of:
    providing dosages of pills from said portable medicine safe.

5. The controlled substance fraud prevention method of claim 1, further comprising the step of:
    providing dosages of liquid from said portable medicine safe.

6. The controlled substance fraud prevention method of claim 1, further comprising the step of:
    providing an external lock to retain said dispensing mechanism in said housing.

7. A controlled substance fraud prevention method comprising the steps of:
    photographing a patient with a camera to obtain a facial image;
    providing a computer server including a database of medicines prescribed to each face and facial recognition software, uploading said facial image with a name to said computer server, said facial recognition software compares said facial image and name with said database of medicines prescribed to each face, said facial recognition software determining if said facial image is associated with more than one of the same prescription to prevent the prescription of the same medicine from multiple doctors for the same patient; and
    providing a portable medicine safe to a patient who has only one name associated with their facial image to prevent the patient from having more than one name associated with the same face in said database of names and faces, said portable medicine safe includes a housing and a dispensing mechanism, a representative of a pharmacy fills said dispensing mechanism with a controlled substance, said dispensing mechanism is locked in said housing, said dispensing mechanism dispenses dosages of the controlled substance.

8. The controlled substance fraud prevention method of claim 7, further comprising the step of:
    said portable medicine safe includes a smart device with a camera, said camera must capture an image of the patient before dispensing a dose of the medicine.

9. The controlled substance fraud prevention method of claim 7, further comprising the step of:
    entering an access code into said smart device to unlock said dispensing mechanism from said housing.

10. The controlled substance fraud prevention method of claim 7, further comprising the step of:
    providing dosages of pills from said portable medicine safe.

11. The controlled substance fraud prevention method of claim 7, further comprising the step of:

providing dosages of liquid from said portable medicine safe.

12. The controlled substance fraud prevention method of claim 7, further comprising the step of:
providing an external lock to retain said dispensing mechanism in said housing.

13. A controlled substance fraud prevention method comprising the steps of:
photographing a patient with a camera to obtain a facial image;
providing a computer server including facial recognition software and a database of names and faces, uploading said facial image with a name to said computer server, said facial recognition software compares said facial image and name with said database of names and faces, said facial recognition software determining if said facial image is associated with more than one name to prevent the patient from having more than one name associated with the same face in said database of names and faces;
providing said computer server with a database of medicines prescribed to each face and facial recognition software, uploading said facial image with a name to said computer server, said facial recognition software compares said facial image and name with said database of medicines prescribed to each face, said facial recognition software determining if said facial image is associated with more than one of the same prescription to prevent the prescription of the same medicine from multiple doctors for the same patient; and
providing a portable medicine safe to a patient who has only one of the same prescription associated with their facial, said portable medicine safe includes a housing and a dispensing mechanism, a representative of a pharmacy fills the dispensing mechanism with a controlled substance, said dispensing mechanism is locked in said housing, said dispensing mechanism dispenses dosages of the controlled substance.

14. The controlled substance fraud prevention method of claim 13, further comprising the step of:
said portable medicine safe includes a smart device with a camera, said camera must capture an image of the patient before dispensing a dose of the medicine.

15. The controlled substance fraud prevention method of claim 13, further comprising the step of:
entering an access code into said smart device to unlock said dispensing mechanism from said housing.

16. The controlled substance fraud prevention method of claim 13, further comprising the step of:
providing dosages of pills from said portable medicine safe.

17. The controlled substance fraud prevention method of claim 13, further comprising the step of:
providing dosages of liquid from said portable medicine safe.

18. The controlled substance fraud prevention method of claim 13, further comprising the step of:
providing an external lock to retain said dispensing mechanism in said housing.

* * * * *